(12) United States Patent
Turowski-Wanke et al.

(10) Patent No.: US 6,448,297 B1
(45) Date of Patent: Sep. 10, 2002

(54) ALKYL PHOSPHATE AND AQUEOUS EMULSIONS THEREOF

(75) Inventors: Angelika Turowski-Wanke, Kelkheim; Matthias Löffler, Niedernhausen, both of (DE)

(73) Assignee: Clariant GmbH, Frankfurt (DE)

( * ) Notice: Subject to any disclaimer, the term of this patent is extended or adjusted under 35 U.S.C. 154(b) by 60 days.

(21) Appl. No.: 09/585,115

(22) Filed: Jun. 1, 2000

Related U.S. Application Data

(63) Continuation of application No. 09/213,654, filed on Dec. 16, 1998, now abandoned.

(30) Foreign Application Priority Data

Dec. 18, 1997 (DE) .......................................... 197 56 373

(51) Int. Cl.[7] .............................. G01F 3/08; G01F 17/14
(52) U.S. Cl. ........................ 516/56; 514/846; 514/939; 516/24; 516/907
(58) Field of Search ........................... 516/56, 24, 907; 514/846, 939; 510/436

(56) References Cited

U.S. PATENT DOCUMENTS

| | | | |
|---|---|---|---|
| 2,822,290 A | | 2/1958 | Webber |
| 3,000,750 A | * | 9/1961 | Felletschin ................ 516/56 X |
| 3,004,056 A | * | 10/1961 | Nunn, Jr. et al. ......... 516/56 X |
| 3,308,161 A | * | 3/1967 | Shen ........................ 516/56 X |
| 3,397,150 A | | 8/1968 | Burt et al. .................. 252/194 |
| 3,807,976 A | | 4/1974 | Polss |
| 3,816,346 A | | 6/1974 | Coppock et al. |
| 4,069,053 A | | 1/1978 | Mayama et al. |
| 4,139,485 A | | 2/1979 | Imokawa et al. |
| 4,191,666 A | * | 3/1980 | Chabert et al. ........... 516/24 X |
| 4,194,988 A | * | 3/1980 | Schneider et al. ............ 516/56 |
| 6,066,753 A | * | 5/2000 | Turowski-Wanke et al. .. 516/56 X |

FOREIGN PATENT DOCUMENTS

| | | |
|---|---|---|
| DE | 2040350 | 3/1971 |
| DE | 2209819 | 9/1972 |
| DE | 2601601 | 7/1976 |
| EP | 0201040 | 11/1986 |
| EP | 0227012 | 7/1987 |
| EP | 0265702 | 5/1988 |
| GB | 1548985 | 7/1979 |
| GB | 2133316 | 7/1984 |
| GB | 2139112 | 11/1984 |
| WO | WO 91/14693 | 10/1991 |

OTHER PUBLICATIONS

PCT Search Report (Apr. 1999).
XP–002097154 "Cetylphosphates As Cosmetic Emulsifiers" K.F. DePolo & G.H. Pittet, Drug Cosmet. Ind., 1989, vol. 145, pp. 26, 28, 30, 34, 82 & 84.

* cited by examiner

*Primary Examiner*—Richard D. Lovering
(74) *Attorney, Agent, or Firm*—Richard P. Silverman

(57) ABSTRACT

The invention relates to alkyl phosphates, in particular their mixtures, of the formula

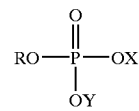

in which R is $C_{12}$–$C_{22}$-alkyl, preferably $C_{14}$–$C_{18}$-alkyl, X is a group of the formulae $NH_3R^1$, $NH_2R^2R^3$ or $NHR^4R^5R^6$, Y is as defined for R or is as defined for X, and $R^1$ is $C_8$–$C_{22}$-alkyl, $R^2$ and $R^3$ are $C_1$–$C_{22}$-alkyl or cyclohexyl, and $R^4$, $R^5$ and $R^6$ are $C_1$–$C_4$-alkyl. These compounds, in particular the mixtures of mono- and diesters, are suitable as emulsifiers in the preparation of aqueous emulsions.

7 Claims, No Drawings

ALKYL PHOSPHATE AND AQUEOUS EMULSIONS THEREOF

CROSS-REFERENCE TO RELATED APPLICATIONS

The present invention is a continuation of application Ser. No. 09/213,654, filed Dec. 16, 1998 and now abandoned, which is hereby incorporated by reference.

FIELD OF THE INVENTION

The invention relates to alkyl phosphates, preferably to their mixtures and to their use as emulsifier, in particular in cosmetic and pharmaceutical emulsions. These esters are notable for being very effective in lowering surface tension, for having high stability, even upon heating, and low sensitivity to electrolytes and acids.

BACKGROUND OF THE INVENTION

The use of emulsifiers for the preparation of creams, lotions, ointments etc., which comprise two or more immiscible substances (e.g. water, oil, organic and inorganic constituents), has been known for a long time. The emulsifiers used are surfactants, e.g. soaps of alkali metals and alkanolamines, mono- and diglyceryl esters of fatty acids, but also certain naturally occurring substances (e.g. lecithins, waxes) and inorganic substances (e.g. bentonites).

EP-B-0 201 040 describes the emulsifying power of metal salts of dialkyl phosphates, and EP-B-0 227 012 that of monoalkyl phosphates in the form of alkali metal salts, amino acid salts or alkanolamine salts.

The phosphates described as emulsifiers in GB-A-2 139 112 and EP-A-265 702 may also be in the form of the alkali metal, amino acid or alkanolamine salts. The use of the $C_1$–$C_3$-alkylammonium salts of these phosphates as emulsifier is described in U.S. Pat. No. 4,139,485.

SUMMARY OF THE INVENTION

It has been found that alkyl phosphates in the form of their fatty alkylamine salts are universally suitable for preparing not only oil-in-water emulsions, but also for water-in-oil emulsions.

The invention provides alkyl phosphates, in particular their mixtures, of the formula

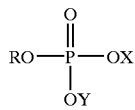

in which R is $C_{12}$–$C_{22}$-alkyl, preferably $C_{14}$–$C_{18}$-alkyl, X is a group of the formulae $NH_3R^1$, $NH_2R^2R^3$ or $NHR^4R^5R^6$, Y is as defined for R or is as defined for X, and $R^1$ is $C_8$–$C_{22}$-alkyl, $R^2$ and $R^3$ are $C_1$–$C_{22}$-alkyl or cyclohexyl, and $R^4$, $R^5$ and $R^6$ are $C_1$–$C_4$-alkyl.

These alkyl phosphates are prepared by processes known per se by reaction of tetraphosphorus decaoxide and fatty alcohols in the approximate molar ratio of 1:1 and subsequent salt formation with an amine of the formulae $NH_2R^1$, $NHR^2R^3$ or $NR^4R^5R^6$, where $R^1$, $R^2$, $R^3$, $R^4$, $R^5$ and $R^6$ are as defined above. This method of preparation produces the phosphates as a mixture of essentially from 30 to 60% by weight of monoester and from 30 to 60% by weight of diester with small amounts of the corresponding triester (from 0 to 10% by weight). The phosphates are preferably in the form of mixtures comprising from 30 to 50% by weight of monoester, from 40 to 60% by weight of diester and from 0 to 2% by weight of triester. The proportions of mono- and diesters are normally approximately equal.

The radical R can be straight-chain or β-branched. Straight-chain fatty alcohols are preferably mixtures of fatty alcohols derived from native fatty acids and are accordingly mixtures of varying chain length and, in addition, also comprise lesser or greater amounts of unsaturated fatty alcohols. The β-branched fatty alcohols are Guerbet alcohols, which are obtainable by the Guerbet synthesis (Ullmann's Encyclopedia of Industrial Chemistry, 5th edition, Vol A 10, p. 288).

Of particular interest are those phosphates in which the radical R is a mixture of branched and unbranched alkyl radicals, for example a mixture of from 0.1 to 5% of β-branched alkyl and from 99.9 to 95% of linear alkyl.

The phosphate mixtures according to the invention are generally suitable for the preparation of surfactant-containing formulations, in which the phosphates are the surfactant. Moreover, these phosphate mixtures are also particularly suitable as emulsifiers for aqueous emulsions of the oil-in-water or water-in-oil type for example emulsions of a cosmetic or pharmaceutical nature, preferably also for the preparation of alcohol-free emulsions. These emulsions comprise the phosphate mixtures according to the invention in amounts of from 0.1 to 5% by weight, preferably from 0.3 to 3% by weight.

The type of emulsion can be influenced by using different types of alkylamines during formation of the salt. For example, long-chain, linear primary alkylamines promote the formation of water-in-oil emulsions, while short-chain branched sec or tert alkylamines promote the formation of oil-in-water emulsions. Such aqueous emulsions containing alkyl phosphate are preferably prepared by heating and homogeneously mixing the constituents of the oil phase together with the mixture of alkyl phosphates in the form of the free acid (i.e. X and Y=H) and the equivalent amount of an alkylamine for the formation of the salt as stated above. The constituents of the aqueous phase are likewise mixed, and oil and aqueous phase are then mixed together with vigorous stirring. The mixture is then stirred until cold. Instead of the pure alkylamine salt, a mixture of alkylamine salt and alkali metal salt may also be present. For this purpose, a substoichiometric amount of alkylamine, based on the alkyl phosphate in the acid form, is used, and the missing amount of base is added in the form of an alkali metal hydroxide. In this way, it is possible to replace up to 75 mol %, in particular up to 25 mol %, of alkylamine with alkali. Instead of alkali, it is also possible to use alkanolamine (e.g. diethanolamine) or basic amino acids (e.g. arginine, lysine or ornithine).

The emulsifiers according to the invention are notable for being very effective in lowering the surface tension, even at high temperatures, of polar and nonpolar constituents. The emulsifiers, some of which are liquid, have improved stability to electrolyte additives and acids and a long shelf life. They have a pH in the range from 5 to 7 and can thus be used as emulsifiers which are very gentle on the skin, both in oil-in-water and water-in-oil emulsions, preferably in skin-care compositions.

The nonaqueous part of the emulsions, which largely comprises the emulsifier and oily substance, is usually from 5 to 95% by weight and preferably from 15 to 75% by weight. This means that the emulsions may comprise from 5 to 95% by weight, and preferably from 25 to 85% by weight, of water, depending on whether the intention is to prepare lotions having a comparatively low viscosity, or creams and ointments having a high viscosity.

Examples of suitable oily substances are Guerbet alcohols having from 6 to 18, preferably from 8 to 10, carbon atoms, esters of linear $C_6$–$C_{13}$-fatty acids with linear $C_6$–$C_{20}$-fatty alcohols, esters of branched $C_6$–$C_{13}$-carboxylic acids with linear $C_6$–$C_{20}$-fatty alcohols, esters of linear $C_6$–$C_{18}$-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on $C_6$–$C_{10}$-fatty acids, vegetable oils, branched primary alcohols, substituted cyclohexanes, Guerbet carbonates, dialkyl ethers and/or aliphatic or aromatic hydrocarbons.

The emulsions can be used as skincare compositions, such as, for example, day creams, night creams, beauty creams, nourishing cream, body lotions, ointments and the like, and may comprise, as further auxiliaries and additives, coemulsifiers, superfatting agents, fats, waxes, stabilizers, biogenic active substances, glycerol, preservatives, dyes and perfumes.

It is essential to the invention that the described mixtures of phosphates can also be used without co-use of a nonionic surfactant as coemulsifier. The co-use of coemulsifiers is thus not imperative, but possible.

Suitable nonionogenic O/W coemulsifiers are the products of the addition reaction of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group; $C_{12}$–$C_{18}$-fatty acid mono- and diesters of the products of the addition reaction of from 1 to 30 mol of ethylene oxide with glycerol; glyceryl mono- and diesters and sorbitan mono- and diesters of saturated and unsaturated fatty acids having from 6 to 22 carbon atoms and the products of their addition reaction with ethylene oxide; products of the addition reaction of from 15 to 60 mol of ethylene oxide with castor oil and/or hydrogenated castor oil; polyol and, in particular, polyglyceryl esters, such as, for example, polyglyceryl polyricinoleate and polyglyceryl poly-12-hydroxystearate. Mixtures of compounds from two or more of these classes of substance are also suitable. The products of the addition reaction of ethylene oxide and/or propylene oxide with fatty alcohols, fatty acids, alkylphenols, glyceryl mono- and diesters and also sorbitan mono- and diesters of fatty acids, or with castor oil, are known products which are available commercially. These are homolog mixtures whose average degree of alkoxylation corresponds to the ratio of the amounts of ethylene oxide and/or propylene oxide and substrate used in the addition reaction. $C_{12}$–$C_{18}$-fatty acid mono- and diesters of products of the addition reaction of ethylene oxide with glycerol are known from DE-20 24 051 as refatting agents for cosmetic preparations.

Refatting agents which can be used are substances such as, for example, polyethoxylated lanolin derivatives, lecithin derivatives, polyol fatty acid esters, monoglycerides and fatty acid alkanolamides, the latter also being used as foam stabilizers. Typical examples of fats are glycerides, and suitable waxes are, inter alia, beeswax, paraffin wax or microwaxes, if desired in combination with hydrophilic waxes, e.g. cetyl stearyl alcohol. Stabilizers which may be used are metal salts of fatty acids, such as, for example, magnesium stearate, aluminum stearate and/or zinc stearate. Biogenic active substances are taken to mean, for example, plant extracts and vitamin complexes. Examples of suitable preservatives are phenoxyethanol, formaldehyde solution, parabens, pentanediol and sorbic acid. Examples of suitable pearlizing agents are glycol distearates, such as ethylene glycol distearate, but also fatty acid monoglycol esters. The dyes which can be used are the substances which are approved and suitable for cosmetic purposes, such as are listed, for example, in the publication "Kosmetische Färbemittel" [Cosmetic Colorants] from the Farbstoffkommission der Deutschen Forschungsgemeinschaft [Dyes Commission of the German Research Society], Verlag Chemie, Weinheim, 1984, pp. 81–106.

The total amount of auxiliaries and additives can be from 1 to 10% by weight, preferably from 2 to 5% by weight, based on the composition.

The compositions can be prepared in a manner known per se, i.e. for example by hot, hot-hot/cold or PIT emulsification.

EXAMPLES

All percentages are by weight.

Example 1

O/W cream, pH 5.5

| | Composition: | |
|---|---|---|
| A | Mixture of mono- and distearylphosphoric acid | 0.50% |
| | Paraffin oil, perliquidum | 10.00% |
| | ® Myritol 318 | 5.00% |
| | ® Cutina GMS | 3.60% |
| | ® Cutina FS 45 | 3.60% |
| | ® Lanette 16 | 0.90% |
| | Dicyclohexylamine | 0.30% |
| | NaOH (10% strength) | 0.50% |
| B | Demin. water | ad 100% |
| | Glycerol 86–88% strength | 5.00% |
| | NaOH 10% strength | q.s. |
| C | ® Euxyl K 400 | 0.15% |
| | Paraffin oil | 0.30% |

Preparation:

Heat phase A to from 80 to 85° C.

Heat phase B to from 80 to 85° C.

Add phase B to phase A with stirring

Stir the resulting emulsion until cold

At about 40° C., add phase C and stir well

At about 30° C., homogenize the emulsion

Example 2

O/W cream, pH 5.5

| | Composition | |
|---|---|---|
| A | Mixture of mono- and distearylphosphoric acid | 0.50% |
| | Paraffin oil perliquidum | 10.00% |
| | Myritol 318 | 5.90% |
| | Cutina GMS | 3.60% |
| | Lanette 16 | 4.50% |
| | Dicyclohexylamine | 0.30% |
| | NaOH (10% strength) | 0.50% |
| B | Demin. water | ad 100% |
| | Glycerol 86–88% strength | 5.00% |
| | NaOH 10% strength | q.s. |
| C | Euxyl K 400 | 0.15% |
| | Paraffin oil | 0.30% |

Preparation:

Heat phase A to from 80 to 85° C.
Heat phase B to from 80 to 85° C.
Add phase B to phase A with stirring
Stir the resulting emulsion until cold
At about 40° C., add phase C and stir well
At about 30° C., homogenize the emulsion

Example 3

Oil-in-water lotion, pH 5.5

| | Composition | |
|---|---|---|
| A | Mixture of mono- and distearylphosphoric acid | 0.50% |
| | Paraffin oil, perliquidum | 10.00% |
| | Myritol 318 | 5.80% |
| | ® Hostacerin DGS | 7.20% |
| | Didecylamine | 0.29% |
| | NaOH (10% strength) | 0.50% |
| | Demin. water | ad 100% |
| | Glycerol 86–88% strength | 5.00% |
| | NaOH 10% strength | q.s. |
| C | ® Euxyl K 400 | 0.15% |
| | Paraffin oil | 0.30% |

Preparation:

Heat phase A to from 80 to 85° C.
Heat phase B to from 80 to 85° C.
Add phase B to phase A with stirring
Stir the resulting emulsion until cold
At about 40° C., add phase C and stir well
At about 30° C., homogenize the emulsion

Example 4

Oil-in-water soft cream, pH 5.5

| | Composition | |
|---|---|---|
| A | Mixture of mono- and distearylphosphoric acid | 0.50% |
| | Paraffin oil, perliquidum | 10.00% |
| | Myritol 318 | 5.90% |
| | Cutina GMS | 3.60% |
| | ® Prisorine 3515 | 4.50% |
| | Didecylamine | 0.29% |
| | NaOH (10% strength) | 0.50% |
| B | Demin. water | ad 100% |
| | Glycerol 86–88% strength | 5.00% |
| | NaOH 10% strength | q.s. |
| C | Euxyl K 400 | 0.15% |
| | Paraffin oil | 0.30% |

Preparation:

Heat phase A to from 80 to 85° C.
Heat phase B to from 80 to 85° C.
Add phase B to phase A with stirring
Stir the resulting emulsion until cold
At about 40° C., add phase C and stir well
At about 30° C., homogenize the emulsion

Example 5

Water-in-oil formulation

| | Composition | |
|---|---|---|
| A | Mixture of mono- and distearylphosphoric acid | 1.00% |
| | Paraffin oil, perliquidum | 12.00% |
| | Myritol 318 | 10.00% |
| | ® Forlan L | 2.00% |
| | ® Lunacera alba | 5.00% |
| | ® Armeen HTD | 0.90% |
| B | Demin. water | 65.65% |
| | Glycerol 86–88% strength | 3.00% |
| C | Euxyl K 400 | 0.15% |
| | Paraffin oil | 0.30% |

Preparation:

Heat phase A to from 80 to 85° C.
Heat phase B to from 80 to 85° C.
Add phase B to phase A with stirring
Stir the resulting emulsion until cold
At about 40° C., add phase C and stir well
At about 30° C., homogenize the emulsion

Example 6

Water-in-oil formulation

| | Composition | |
|---|---|---|
| A | Mixture of mono- and distearylphosphoric acid | 1.00% |
| | Paraffin oil, perliquidum | 12.00% |
| | Myritol 318 | 12.00% |
| | Forlan L | 2.00% |
| | Lunacera alba | 1.00% |
| | ® Elfacos ST 9 | 2.00% |
| | ® Genamin 18 R 100 D | 0.70% |
| B | Demin. water | 65.85% |
| | Glycerol 86–88% strength | 3.00% |
| C | Euxyl K 400 | 0.15% |
| | Paraffin oil | 0.30% |

Preparation:

Heat phase A to from 80 to 85° C.
Heat phase B to from 80 to 85° C.
Add phase B to phase A with stirring
Stir the resulting emulsion until cold
At about 40° C., add phase C and stir well
At about 30° C., homogenize the emulsion List of commercial products used:

| | |
|---|---|
| Paraffin perliquidum (Wagner, Bremen) | Mineral oil |
| Myritol 318 (Henkel, Düsseldorf) | Capric/Caprylic triglyceride |
| Cutina GMS (Henkel) | Glyceryl stearate |
| Cutina FS (Henkel) | Palmitic acid, stearic acid |
| Lanette 16 (Henkel) | Cetyl alcohol |
| Lanette O (Henkel) | Cetearyl alcohol |
| Hostacerin DGS (Clariant) | Polyglycerol-2 PEG-4 stearate |
| Prisorine 3515 (Unichema) | Isostearyl alcohol |
| Glycerol 86 to 88% (Henkel) | Glycerol |
| Euxyl K 400 (Schülke + Mayr) | Methyldibromoglutaronitrile |

| | -continued |
|---|---|
| Forlan L (Erbslöh, Krefeld) | Lanolin, hydrogenated coconut oil, sorbitan sesquioleate, stearyl alcohol, cetyl alcohol |
| Lunacera alba (Fuller, Lüneburg) | Cera alba |
| Armeen HTD (Akzo, Düren) | Hydrogenated tallow fatty amine |
| Elfacos ST 9 (Akzo, Düren) | PEG-45/dodecyl glycol copolymer |
| Genamin 18R 100D (Clariant) | Octadecylamine |

What is claimed is:

1. An alkyl phosphate of the formula

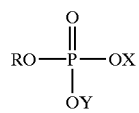

in which R is a mixture of from 0.1 to 5 weight percent of β-branched $C_{12}$–$C_{22}$-alkyl and from 99.9 to 95.0 linear $C_{12}$–$C_{22}$ alkyl, X is a group of the formulae $NH_3R^1$, $NH_2R^2R^3$ or $NHR^4R^5R^8$, Y is as defined for R or is as defined for X, and $R^1$ is $C_8$–$C_{22}$-alkyl, $R^2$ and $R^3$ are $C_1$–$C_{22}$-alkyl or cyclohexyl, and $R^4$, $R^5$ and $R^6$ are $C_1$–$C_4$-alkyl.

2. A mixture of alkyl phosphates as claimed in claim 1, which comprises from 0 to 10% by weight of the corresponding triester.

3. A mixture of alkyl phosphates as claimed in claim 1, wherein the linear $C_{12}$–$C_{22}$ alkyl portion of R is $C_{14}$–$C_{18}$ alkyl.

4. A mixture of alkyl phosphates as claimed in claim 1, wherein X and Y are $C_{14}$–$C_{18}$-alkylammonium.

5. An aqueous emulsion comprising an alkyl phosphate as claimed in claim 1.

6. An aqueous emulsion comprising from 0.1 to 5% by weight of an alkyl phosphate as claimed in claim 1.

7. An aqueous emulsion comprising an alkyl phosphate as claimed in claim 1, wherein X and/or Y is a mixture of $C_{12}$–$C_{22}$-alkylammonium and alkali metal cation.

* * * * *